United States Patent
Ponsati I Obiols et al.

(10) Patent No.: US 6,897,289 B1
(45) Date of Patent: May 24, 2005

(54) PEPTIDE SYNTHESIS PROCEDURE IN SOLID PHASE

(75) Inventors: Berta Ponsati I Obiols, Barcelona (ES); Marc Canas I Poblet, Barcelona (ES); Gemma Jodas I Farres, Barcelona (ES); Javier Clemente Rodriguez, L' Hospitalet de Llobregat Barcelona (ES); Jordi Barcadit I Cabado, Sant Celoni Barcelona (ES)

(73) Assignee: Lipotec, S.A. (ES)

( * ) Notice: Subject to any disclaimer, the term of this patent is extended or adjusted under 35 U.S.C. 154(b) by 0 days.

(21) Appl. No.: 09/979,293

(22) PCT Filed: May 5, 2000

(86) PCT No.: PCT/ES00/00169

§ 371 (c)(1),
(2), (4) Date: Nov. 20, 2001

(87) PCT Pub. No.: WO00/71570

PCT Pub. Date: Nov. 30, 2000

(30) Foreign Application Priority Data

May 20, 1999 (ES) ............................................... 9901090

(51) Int. Cl.$^7$ ............................ C07K 1/06; A61K 38/08
(52) U.S. Cl. ......................... 530/333; 530/338; 530/337
(58) Field of Search ................................ 530/335, 328, 530/334, 337, 338

(56) References Cited

U.S. PATENT DOCUMENTS

| | | | |
|---|---|---|---|
| 4,024,248 A | 5/1977 | Konig et al. ................. | 424/177 |
| 4,100,274 A | 7/1978 | Dutta et al. .................. | 424/177 |
| 5,455,363 A | 10/1995 | Gosteli et al. .............. | 552/104 |
| 5,602,231 A | * 2/1997 | Cotton et al. ............... | 530/334 |

FOREIGN PATENT DOCUMENTS

| | | |
|---|---|---|
| CH | 682662 | 10/1993 |
| DE | 4306839 | 9/1994 |
| EP | 0475184 | 3/1992 |
| EP | 0518655 | 12/1992 |
| EP | 0518656 | 12/1992 |
| GB | 1524747 | 9/1978 |
| IE | 913051 | 3/1992 |

OTHER PUBLICATIONS

Lloyd–Williams et al., "Convergent Solid–Phase Peptide Synthesis", 1993, in Tetrahedron, 49(48), pp. 11065–11133.*

Alberico et al., "Convergent Solid–Phase Peptide Synthesis", 1997, in Methods in Enzymology, vol. 289, Chapt. 15, pp313–336, ed. Fields, Academic Press, New York.*

A. Friedrich et al., "Experiences During the Development of the Buserelin Acetate Synthesis," Peptides 1992, pp. 47–49 (C.H. Schneider and A.N. Eberle, Eds.), 1993 ESCOM Science publishers B.V.

* cited by examiner

Primary Examiner—Robert A. Wax
Assistant Examiner—Suzanne M. Mayer
(74) Attorney, Agent, or Firm—Ostrolenk, Faber, Gerb & Soffen, LLP

(57) ABSTRACT

A procedure for the solid phase peptide synthesis (SPPS), following a linear or convergent strategy, wherein the peptides contain the sequence of general formula (I), wherein n, Y, X and $A_1$ to $A_n$ have the meanings indicated in the specification. Said procedure comprises: the use of amino acids with the Nα group protected, protecting the side chains of those amino acids that have their side chain alkylated or acylated in the final product with labile protecting groups, protecting the side chains of at least one of the amino acids that has its chain free in the final product with hyperlabile products and using a polymeric support which provides labile peptide-resin bonds.

Said procedure is valid for the synthesis of gosereline and busereline $$Y-A_1-A_2-A_3-\ldots A_{(n-1)}-A_n-X.$$

11 Claims, 5 Drawing Sheets

PEPTIDE SYNTHESIS PROCEDURE IN SOLID PHASE

BACKGROUND OF THE INVENTION (1) Field of the Invention

The present invention relates to a procedure for solid phase peptide synthesis (SPPS), following a linear or convergent strategy, wherein the peptides contain the sequence of general formula (I):

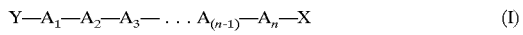

$$Y-A_1-A_2-A_3- \ldots A_{(n-1)}-A_n-X \quad (I)$$

as well as all pharmaceutically acceptable salts for the peptide formed by the addition of acids or complexes thereof, wherein:

30>n>1

Y=H—, $(C_1-C_{20})$ alkyl or $(C_1-C_{20})$ acyl;

X=—OH, —NHCH$_3$, —NHCH$_2$CH$_3$, —NH—C$_a$H$_b$ (10>a>2 and 18>b>5), —NHCF$_3$, —NHCH$_2$CF$_3$, —NH—C$_a$H$_b$F$_f$ (10>a>2, 18>b>5, 9>f>0), —NH—C$_c$H$_d$O$_e$ (c, d and e>1) or —NH—NR—CO—NH$_2$ (where R represents the side chains of any amino acid);

$A_n$ (30>n>1) can be any natural of synthetic amino acid, including pyroglutamic acid, provided the sequence contains a minimum of one amino acid with the side chain acylated or alkylated, with a tert-butyl or tert-butoxycarbonyl group for example;

using, should it be necessary, temporary protector groups labile to treatments with basic solutions for the Nα groups of the amino acids during synthesis.

(2) Description of Related Art

The procedure of the invention, the result of a combination of protocols, is characterised by the type of polymeric supports used which are insoluble in organic solvents and which provide a peptide resin bond which is labile in acid solutions of type 1 (see table 1), such as resins of the chlorotrityl, trityl, methyltrityl or methoxytrityl type for example. Said procedure is also characterised by the type of side chain protectors, labile or hyperlabile to treatment with acid, used for the different tri-functional amino acids that the sequence contains. The different degrees of lability of said protectors of the side group with respect to type 1 and/or type 2 acidolytic treatments (see table 1) allow said protectors to be eliminated or maintained in selective fashion.

TABLE 1

| Type | Acid Solutions |
|---|---|
| 1 | Acetic acid in proportions ranging from 1 to 30% in various solvents, or hexafluoroisopropanol in variable concentrations in different solvents or equivalent acid solutions. |
| 2 | Acetic acid in proportions greater than 30% in different solvents, or trifluoroacetic acid in proportions lower than 5% in different solvents or equivalent acid solution |

In accordance with the invention, the peptides of general formula (I) are synthesised using SPPS by a procedure characterised by the use of a polymeric support which allows the peptide to be cleaved from the peptidyl-resin using type 1 acid solutions (see table 1). Said procedure is also characterised by the use of labile protectors and hyperlabile protectors which can be selectively removed by treatments of with acids of type 1 or 2 (see table 1).

Thus, for the side chain of those tri-functional amino acids in which said chain will be alkylated or acylated in the final product, protectors stable to treatment with acids of type 1 or 2 are used. On the other hand, for the side chain of at least one of the tri-functional amino acids, which has the chain free in the final product, hyperlabile groups are used (labile to treatments with acids of type 2, but stable to treatment with acids of type 1, see table 1) as those used for breaking the peptide-resin bond. This characteristic of the aforementioned protectors allows peptides of general formula I (X≠OH) to then be obtained by derivatisation at the C-terminus, with very good yields, of synthetic intermediates that may have all or some of the side chains of the tri-functional residues protected.

The abbreviations used in the present description have the following meanings:

AcOH: acetic acid
Arg: L-arginine
AzaGly: Azaglycine
Boc: tert-butoxycarbonyl
Bzl: benzyl
ClTrt: Chloro-trityl
DCM: dichloromethane
DIEA: N,N'-diisopropylethylamine
DIPCDI: diisopropylcarbodyimide
DMF: N,N-dimethylformamide
D-Ser: D-serine
Fmoc-aa: Fmoc-amino acid
Fmoc: 9-fluorenylmethoxycarbonyl
His: L-histidine
HOBT: 1-hydroxybenzotriazol
HPLC: high performance liquid chromatography
Ile: L-isoleucine
Leu: L-leucine
LH-RH: Luteinising hormone release hormone
Mmt: Methoxytrityl
NO$_2$: nitro
Pip: piperidine
Pro: L-proline
PyBOP: Benzotriazol-1-yl-oxy hexaflourophosphate
Pyr: pyroglutamic acid
Ser: L-serine
SPPS: Solid phase peptide synthesis
t-Bu: Tert-butyl
TFA: trifluoroacetic acid
Trp: L-tryptophane
Trt: Trityl
Try: L-tyrosine
Z: benzyloxycarbonyl The synthesis methods, described in the state of the art, for the peptides that retain the side chain of at least a tri-functional residue acylated or akylated in the final product, can be divided into two strategies. The first of these strategies condenses free peptide fragments or protected fragments in solution, using classical peptide synthesis schemes well known in the art as well as temporary groups labile to hydrogenolysis and protectors of side chains also labile to hydrogenolysis. The second of the strategies is based on the use of SPPS procedures, employing different polymeric supports and protector groups. One of these strategies is characterised because the synthesis is carried out without protection for the side chains of the tri-functional amino acids that are free of derivatisation in the final products.

The main difficulty involved in the synthesis of compounds of formula (I) lies in the simultaneous presence of residues that should retain their protectors and other residues whose chains should be free in the final product. The most conflictive case is when the peptide contains two or more residues repeated, some of which contain the alkylated or acylated side chain in the final product while others should remain free of alkylation or acylation in the final product.

We shall now review the methods described in the state of the art for the synthesis of products of general formula (1), in particular, goserelina and busereline.

1. Synthesis in Solution, Condensation of Fragments

The patents U.S. Pat. No. 4,100,274 and U.S. Pat. No. 4,024,248 describe methods for synthesis of gosereline and busereline, respectively, by means of condensation of fragments in solution. Both methods are based on the coupling of previously synthesised peptide fragments, mostly with unprotected side chains (see FIG. 1 and FIG. 2), to arrive at the final product with very low yields (lower than 5% with respect to the starting materials) according to that deduced from the examples presented in the specification of said patents.

The method described in U.S. Pat. No. 4,100,274 obtains gosereline by means of the condensation of three pre-formed fragments which contain —$NO_2$ as the protecting group for arginine and -Bzl as the protecting group for tyrosine, both of which are labile to hydrogenolysis. In this method the azaglycine residue is introduced into the C-terminus tripeptide (H-Arg($NO_2$)Pro-AzGly is synthesised) which is then coupled to Z-Tyr(Bzl)-D-Ser(tBu)-Leu-$N_3$, to give a fragment which, once the Z group is removed, couples to Pyr-His-Trp-Ser-$N_3$ to give gosereline. This last reaction is carried out with all the side chains unprotected with the exception of that belonging to D-Ser(tBu) which possibly leads to the appearance of numerous products with acylation of side chains which must then be hydrolysed with the corresponding reduction in yield.

The literature [Frederich A., Jager G., Radschmit K., Ullman R., Peptides 1992 (Schneider C. H. and Eberle A. E. Eds) 1993 Escom Science Publishers (The Netherlands)] as well as the patent U.S. Pat. No. 4,024,248 describe a method for obtaining busereline (see FIG. 2) analogous to that described for gosereline in U.S. Pat. No. 4,100,274. The only difference lies in the fact that in this case the first fragment to be synthesised has an ethylamide terminus instead of the azaGly residue [H-Arg($NO_2$)-Pro-NH—$CH_2CH_3$].

The patent ES458691, belonging to the same family as the patents U.S. Pat. No. 4,100,274 and U.S. Pat. No. 4,024,248 discloses a method for synthesis of gosereline and busereline in solution by condensation of fragments analogous to those disclosed in the aforementioned American patents. Said patent uses a scheme of side-chain protectors for the tri-functional amino acids which is based on the different lability thereof with respect to hydrogenolysis.

2. Solid-Phase Synthesis

There are three patents that disclose solid phase peptide synthesis (SPPS) methods.

The patent EP 0518656A2 carries out the synthesis of Gosereline on a OBzl-polystyrene resin which is labile to hydrazine, obtaining a derivatization of the hydrazide type during the breakage of the peptide-resin bond at the C-terminus which can later be transformed into the azaglycine terminus residue. Said procedure uses the tert-butoxycarbonyl and fluorenylmethoxycarbonyl groups as temporary protectors of the $N\alpha$ group of the amino acids, while for the side chains of the amino acids the following protector groups are used: BrZ for Tyr, Fmoc for His and tBu for D-Ser at the 6 position avoiding the protection of the Ser at position 4 to then convert the hydrazide end into AzaGly-NH2 by reaction KCN after breakage of the peptide-resin bond and deprotection of the side chains. The examples described in the specification do not permit an objective evaluation of the yield that is obtained from the process.

On the other hand, the patent EP 0518655A2 carries out a solid-phase synthesis using a linear strategy starting with the coupling on a peptidyl-resin derivatised with the bi-functional spacer (Rink amide) of AzaGly with no protection for the Tyr and Ser side chains at the 4 position. This process requires that the final peptide be treated with hydrazine to hydrolyse possible side products with acylated amino-acid side chains which are incorporated in free form. This procedure provides an overall yield after purification of 30% according to that deduced from the examples described in the specification of said patent.

The European patent EP 0475184A1 discloses a method for the synthesis of different peptides, among which gosereline can be found, based on the synthesis in solution of Boc-Pro-AzaGly-Bifunctional spacer which is coupled to a polymeric support. With the peptidyl-resin obtained the synthesis continues following a linear strategy with Fmoc-t-Bu strategy. The final step consists of deprotecting the side chains with TFA:ethandithiol (90:10, v/v).

The procedure object of the present invention allows, among other things, the peptides disclosed in the aforementioned patents to be produced with better yields and provides the following synthesis methods that can easily be scaled up, from a common precursor that can be synthesised in bulk.

The appearance during the 90s of hyperlabile protectors allows the synthesis of said derivatives according to an innovative method which is advantageous in that:

The growth of the peptide chain is carried out in solid phase following a completely linear strategy, with better yields than those described up until present and which allows totally or partially protected (X=OH) peptides to be obtained which may be derivatised at the C-terminus with very good yields and using not very aggressive methods common in the art and which do not lead to the formation of large quantities of epimerisation side products.

Elimination of the protectors from the side chain of the tri-functional amino acids is carried out using methods, orthogonal to those used for breaking the peptide-resin bond, with excellent yields and which are less aggressive that those described up until present (treatments with type-2 acid solutions compared to hydrogenolysis or treatments with hydrazine described previously). This fact helps in the industrial scale-up of the process.

BRIEF SUMMARY OF THE INVENTION

The procedure of the present invention presents some clear advantages with respect to the methods already described. The overall yield of the process, 38–45%, makes it a viable process on an industrial scale. The combination of labile and hyperlabile protectors allows the synthesis to be carried out following a linear strategy while in the processes already described it was necessary to carry out the synthesis by condensation of fragments. Similarly, when it is a question of peptides derivatised at the C-terminus, the synthesis described in the solid phase incorporate a suitable functional group into the polymeric support to thus obtain the derivatised peptide on breaking the peptide-resin bond. The procedure of the present invention allows the precursors to be obtained in solid phase either totally or partially protected by derivatisation thereof so that, after the appropriate deprotection, the final product is obtained. The combination of labile and hyperlabile protectors for the side chains of the tri-functional amino acids allows the industrial scale-up of the process with the use of minimal quantities of acids and without the use of hydrogenolysis or treatments with hydrazine or other toxic reagents.

DETAILED DESCRIPTION OF THE INVENTION

The procedure of the present invention consists of the synthesis in solid phase of peptides of general formula (I), following a linear or convergent strategy, which has at least one residue whose side chain is alkylated or acylated;

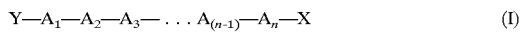

$$Y—A_1—A_2—A_3— \ldots A_{(n-1)}—A_n—X \quad (I)$$

as well as all pharmaceutically acceptable salts for the peptide formed by the addition of acids or complexes thereof, wherein:

30>n>

Y=H—, ($C_1$–$C_{20}$) alkyl or ($C_1$–$C_{20}$) acyl;

X=OH, —$NHCH_3$, —$NHCH_2CH_3$, —NH—$C_aH_b$ (10>a>2 and 18>b>5), —$NHCF_3$, —$NHCH_2CF_3$, —NH—$C_aH_bF_f$ (10>a>2, 18>b>5, 9>f>0), —NH—$C_cH_dO_e$ (c, d and e>1) or —NH—NR—CO—$NH_2$ (where R represents the side chains of any amino acid);

$A_n$ (30>n>1) can be any natural of synthetic amino acid, including pyroglutamic acid, provided the sequence contains a minimum of one amino acid with the side chain acylated of alkylated, with a tert-butyl or tert-butoxycarbonyl group for example;

characterized because it comprises:

a) the use of amino acids with the Nα group protected, through the use of temporary protector groups labile to treatment with basic solutions.

b) protecting the side chains of those amino acids which have the chain alkylated or acylated in the final product, with labile protectors (stable to acid solutions of type 1 and 2 indicated below).

| Type | Acid Solutions |
|---|---|
| 1 | Acetic acid in proportions ranging from 1 to 30% in various solvents, or hexafluoroisopropanol in variable concentrations in different solvents or equivalent acid solutions. |
| 2 | Acetic acid in proportions greater than 30% in different solvents, or trifluoroacetic acid in proportions lower than 5% in different solvents or equivalent acid solution | c) protecting the side chains of at least one of the amino acids that has the chain in free form in the final product, with hyperlabile protectors (stable to treatment with acid solutions of type 1 and labile to treatment with acid solutions of type 2 indicated above) and d) using a polymeric support that provides peptide-resin bonds which are labile to treatment with acid solutions of type 1 indicated earlier.

Figure 1:
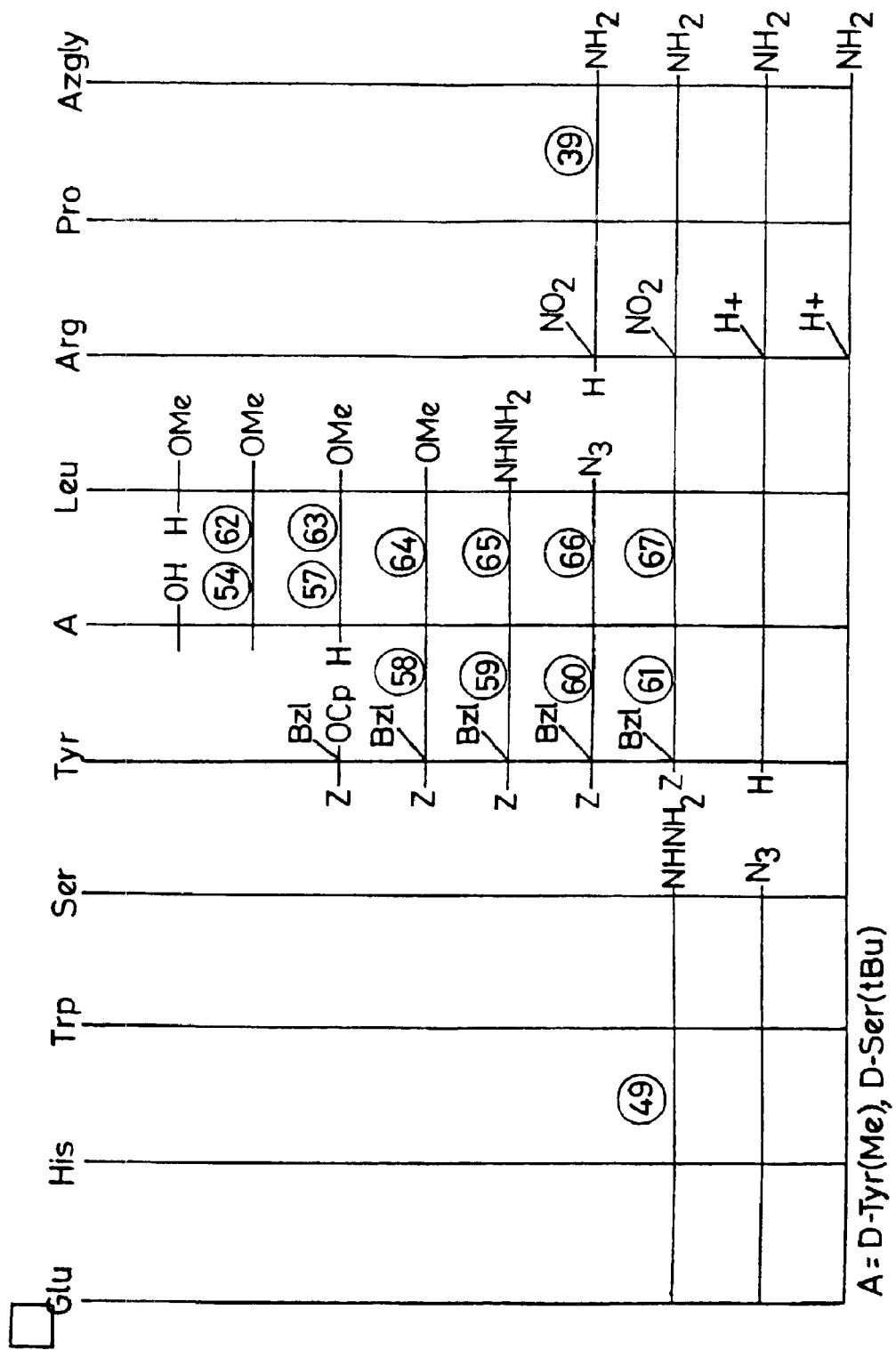
FIG. 1 illustrates the synthesis scheme (in solution) for gosereline as described in U.S. Pat. No. 4,100,274.
Figure 2:
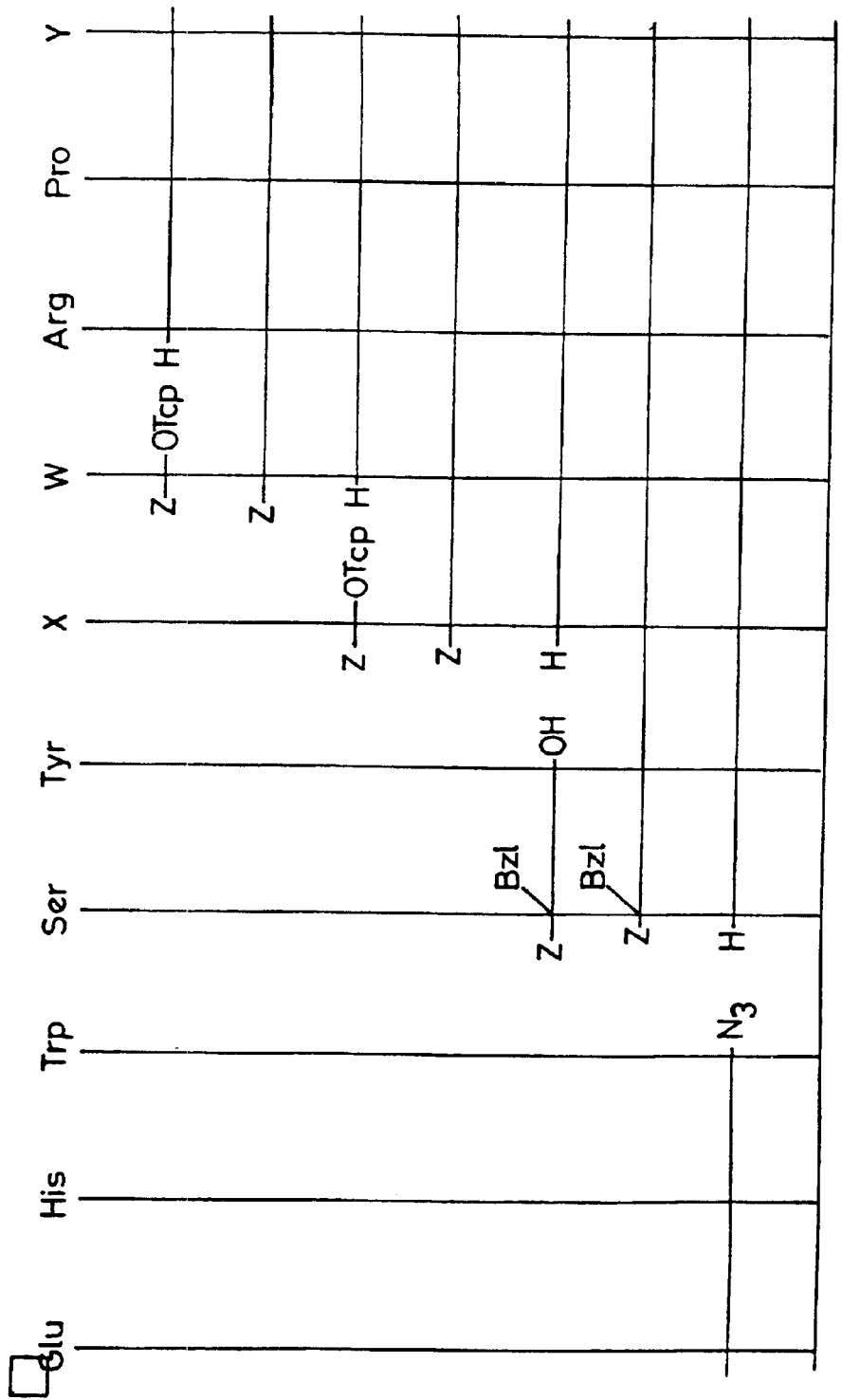
FIG. 2 illustrates the synthesis scheme (in solution) for busereline as described in U.S. Pat. No. 4,024,248.
Figure 3:
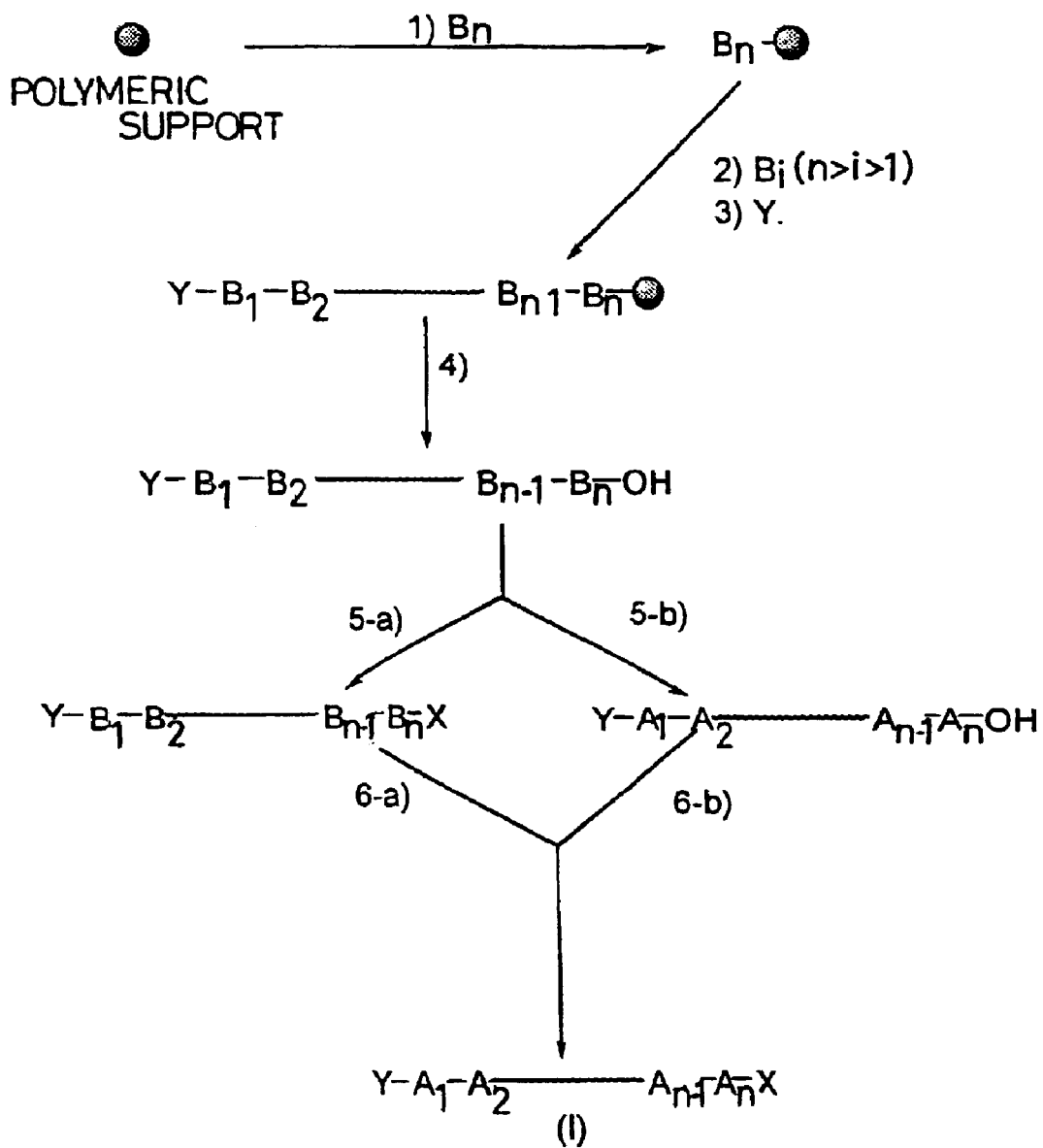
FIG. 3 illustrates the general solid phase synthesis procedure in accordance with the invention for obtaining peptides with both protected and non-protected side chains in the final step, such as gosereline and busereline for example.

When developed, the procedure of the invention, schematised in FIG. 3, comprises the following steps:

1) Incorporation of the first amino acid $B_n$ onto the polymeric support through the use of conventional coupling methods commonly used in the art;

2) Posterior elongation of the peptide chain through the incorporation of $B_i$ (n>i>1) through the use of conventional coupling methods commonly used in the art;

3) Incorporation of the Y group (substituent at the N-terminus of the peptide);

4) Breakage of the peptide-resin bond with type-1 acid solutions;

5) a) Incorporation of the X group through the use of conventional methods known in the art or, alternatively; b) Elimination of the hyperlabile groups protecting the side chains of those tri-functional residues which contain such protecting groups through treatment with type-2 acid solutions;

6) a) Elimination of the hyperlabile protector groups of the those tri-functional residues which contain such groups through treatment with type-2 acid solutions or alternatively; b) Incorporation of the X group through the use of conventional methods known in the art.

In both the scheme shown in FIG. 3 and the description of the synthesis steps:

$A_i$ (from i=1 to i=n), X and Y are residues previously described in the general formula I.

$B_i$ (from i=1 to i=n)=$A_i$ (from i=1 to i=n) for those non tri-functional residues or for those tri-functional residues that have been incorporated with the free side chain, or $B_i$ (from i=1 to i=n) is the same residue as $A_i$ (from i=1 to i=n) with additional protection in the side chain through the use of hyperlabile groups for those amino acids that have the chain free in the final product but which are incorporated with it protected, or $B_i$ (from i=1 to i=n) is the same residue as $A_i$ (from i=1 to i=n) with additional protection in the side chain through the use of labile groups for those amino acids which have their chain alkylated or acylated in the final product.

The hyperlabile protectors used for the side chains of some amino acids are preferably methyltrityl, methoxytrityl or trityl for histidine, trityl or chlorotrityl for tyrosine, methyltrityl or trityl for lysine and trityl for aspartic acid, glutamic acid, threonine, serine, asparagine or glutamine.

The labile protectors of those amino acids whose side chain remains protected in the final product are preferably tert-butyl or tert-butoxycarbonyl.

The polymeric supports which provide peptide-resin bonds labile to treatment with said type-1 acid solutions, are preferably resins of the chlorotrityl, trityl, methyltrityl or methoxytrityl type.

According to a modality of the invention, for the preparation of the peptides of general formula (I) where X=OH, the procedure comprises the following steps:

i) Incorporation of the first amino acid conveniently protected onto the polymeric support through the use of conventional coupling methods commonly used in the art;

ii) Linear growth of the peptide chain using hyperlabile protectors for the side chains of at least one of those amino acids that has its chain free in the final product and labile protector(s) for the amino acid(s) that is/are alkylated or acylated in the final product; and iii) Breakage of the peptide-resin bond through treatment with type-1 acid solutions to obtain the protected precursor.

According to another modality, for the preparation of peptides of general formula (I) in which X is not OH, the procedure of the invention comprises the same steps as when X=OH, and additionally the following steps:

iv) Conversion of the precursor, which contains labile and hyperlabile protecting groups on the lateral chains of some amino acids, to give rise to the final protected product; and v) Elimination of the hyperlabile protecting groups present in the peptide by means of treatment with type-2 acid solutions to obtain the final product.

According to another modality, for the preparation of peptides of general formula (I) in which X is not OH, the procedure of the invention comprises the same steps as when X=OH, and additionally the following steps:

v) Elimination of the hyperlabile protecting groups present in the peptide by means of treatment with type-2 acid solutions to obtain the final product; and iv) Conversion of the precursor, which only contains labile protecting groups on the lateral chains of some amino acids, to give rise to the final protected product.

In accordance with the modalities expressed above, the present invention provides, as an additional aspect thereof, procedures for the synthesis of gosereline and busereline. Thus, for the synthesis of gosereline, the procedure of the invention comprises the following steps:

i) Coupling of Fmoc-Pro-OH onto the resin 2-chlorotrityl and subsequent linear growth of the peptide chain through coupling of Fmoc-Arg(HCl), Fmoc-Leu, Fmoc-D-Ser(tBu), Fmoc-Tyr(ClTrt), Fmoc-Ser(Trt), Fmoc-Trp, Fmoc-His(Mmt) and pyroglutamic acid;

ii) Breakage of the peptide-resin bond through treatment with type-1 acid solutions to obtain the protected precursor;

iii) Elimination of the hyperlabile protecting groups present in the protected precursor through treatment with type-2 acid solutions; and iv) Conversion of the precursor through formation of an active ester thereof and subsequent coupling of semicarbacide to give rise to gosereline.

In the given case, the gosereline synthesis procedure can be interrupted at step ii) and the following steps followed:

iii) Conversion of the precursor, with all or some of the tri-functional amino acids which will have the free side chain in the final product protected, through formation of an active ester thereof and subsequent coupling of semicarbacide to give rise to protected gosereline; and iv) Elimination of the hyperlabile protecting groups present in the protected gosereline through treatment with type-2 acid solutions.

With regards the synthesis of busereline, the procedure of the invention comprises the following steps:

i) Coupling of Fmoc-Pro-OH onto the 2-chlorotrityl resin and subsequent linear growth of the peptide chain through coupling of Fmoc-Arg(HCl), Fmoc-Leu, Fmoc-D-Ser(tBu), Fmoc-Tyr(ClTrt), Fmoc-Ser(Trt), Fmoc-Trp, Fmoc-His(Mmt) and pyroglutamic acid;

ii) Breakage of the peptide-resin bond through treatment with type-1 acid solutions to obtain the protected precursor;

iii) Elimination of hyperlabile protecting groups present in the protected precursor through treatment with type-2 acid solutions; and iv) Conversion of the precursor through formation of an active ester thereof and subsequent coupling of the salt of HOBt of ethylamine to give rise to busereline.

Similarly, the busereline synthesis procedure indicated above can be interrupted at step ii) and the following steps carried out:

iii) Conversion of the precursor, with all or part of the tri-functional amino acids which the side chain will have free in the final product, through the formation of an active ester thereof and subsequent coupling of the HOBt salt of the ethylamine to give rise to the protected busereline; and iv) Elimination of the hyperlabile protecting groups present in the protected gosereline through treatment with type-2 acid solutions.

The synthesis of gosereline and busereline by this procedure will now be presented, as non-limiting examples, to give a detailed illustration of the combination of protectors described in the present application.

Figure 4:
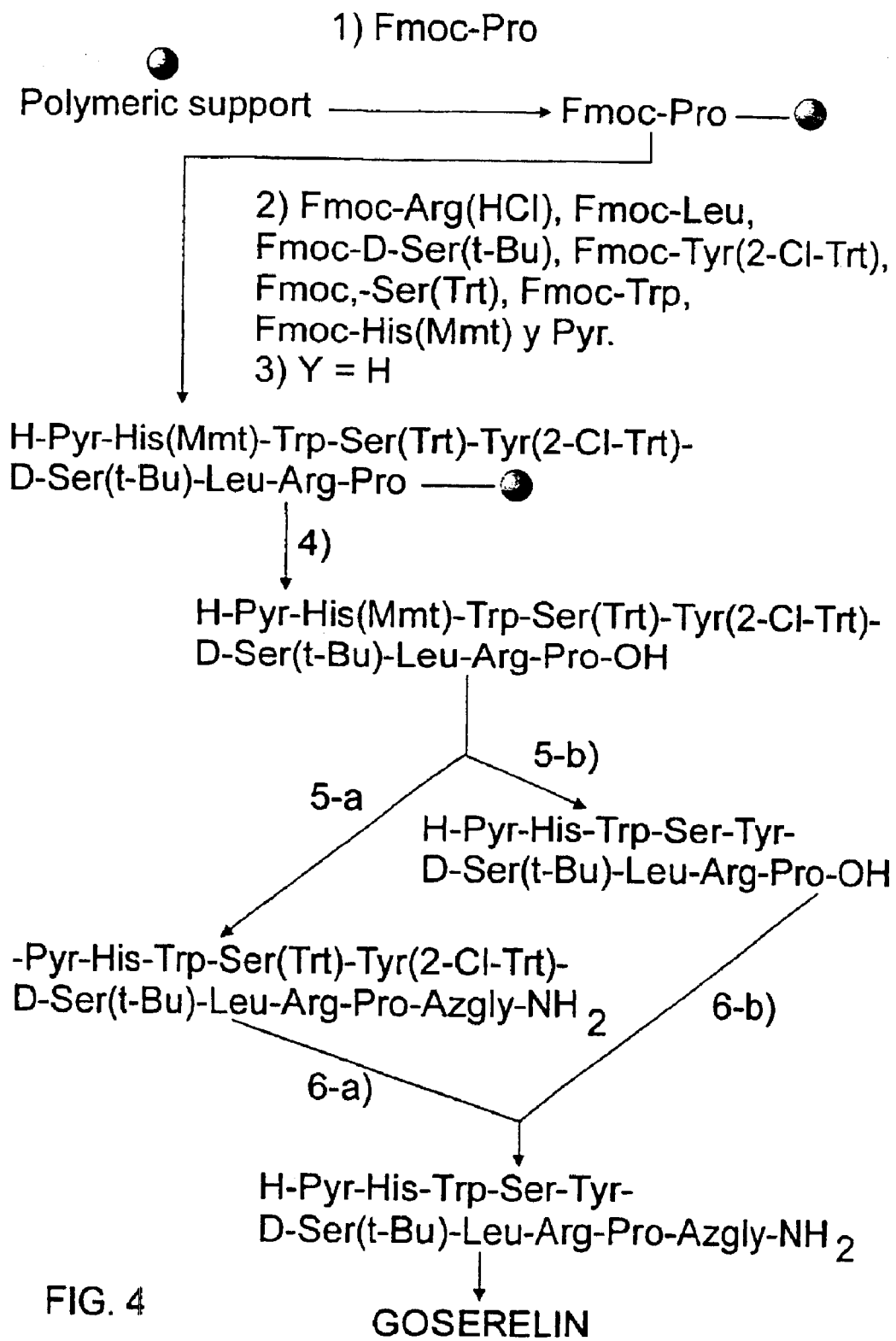
FIG. 4 illustrates a solid phase synthesis procedure in accordance with the invention as used in producing gosereline.
Figure 5:
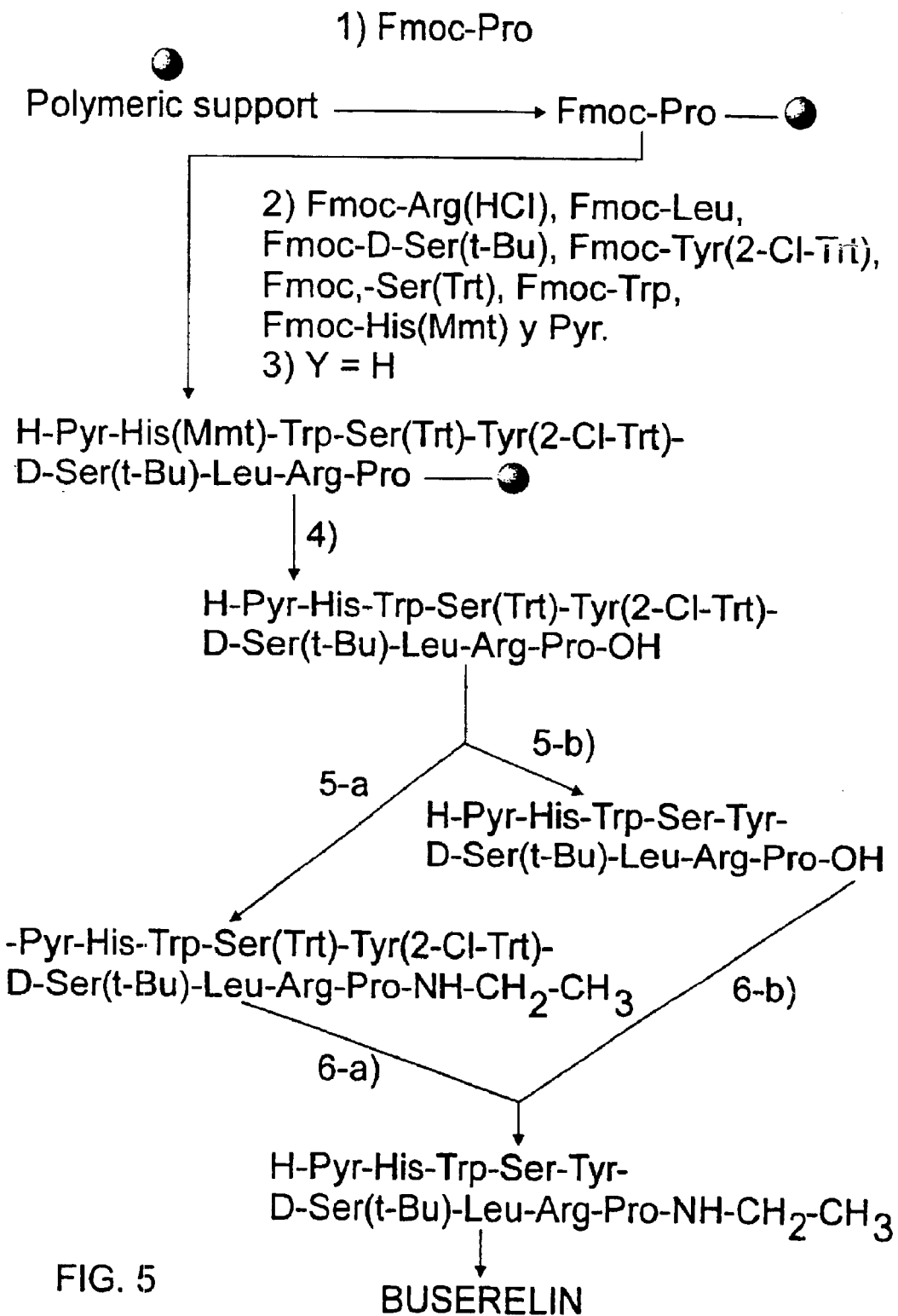
FIG. 5 illustrates a solid phase synthesis procedure in accordance with the invention as used in producing busereline.

As examples of the use of the synthesis protocol described in the present invention, the production of gosereline in FIG. 4 and busereline in FIG. 5 is described.

EXAMPLE 1

Formation of FmocArg(HCl)

50 g of FmocArgOH (110 mmols) are dissolved with an equivalent quantity of 1N HCl. The solution is filtered through 10 μm nylon filters. The mixture is frozen in a dry-ice/acetone bath and lyophilised until completely dry. Quantitatively 47.52 g of Fmoc-ArgHCl are obtained.

EXAMPLE 2

Incorporation of the First Amino Acid. Formation of an Ester Bond Between FmocPro and the 2-chlorotrityl Resin.

Programme for the incorporation of the first amino acid Fmoc Pro (1).
f = 1.35    200 g resin    Excess 1    MW 337.4

| Step | Reagent | Repetitions | Time |
|---|---|---|---|
| 1 | Fmoc aa (1 eq) | | 91.1 g |
|   | DIEA (2.5 eq) | | 116 mL |
|   | When the coupling time is up add 160 mL of MeOH (0.8 mL/g resin) | | 5' |
| 2 | DCM | 3 | 1' |
| 3 | DMF | 5 | 1' |
| 4 | 5% pip/DCM:DMF 1:1 | 1 | 1' |
| 5 | 20% pip/DMF | 1 | 15' |
| 6 | DMF | 5 | 1' |

Dissolve 91.1 g (270 mmol) of Fmoc-Pro-OH (dried for 12 h under vacuum in the presence of KOH) in 2000 mL dry DCM over molecular sieves (10 mL per gram of resin). Once the amino acid has dissolved ⅓ of the DIEA (38.6 mL) are added and everything is thrown over the resin (dried for 12 hours under vacuum in the presence of OH). The mixture is left to react for five minutes. After this time is up the remaining ⅔ of the DIEA (77.3 mL) in DCM 1:1 (77.3 mL of DCM) are added. The reaction is left to run for 40 minutes with vigorous shaking.

160 mL of HPLC grade MeOH (0.8 mL per gram of resin) is added and left shaking for 5 minutes, with the aim of blocking the remaining hydroxyl groups.

EXAMPLE 3

Incorporation of Different Amino Acids. Production of Pyr-His(Mmt)-Trp-Ser(Trt)-Tyr(2ClTrt)-D-Ser(tBu)-Leu-Arg-Pro-Resin 2-Cl-Trt

| Step | Reagent | Repetitions | Time |
|---|---|---|---|
| Programme for incorporation of Fmoc-Arg(HCl)—OH (2) f = 0.85    200 g resin    Excess 9 eq.    MW 433 | | | |
| 1 | DMF | 3 | 1' |
| 2 | Fmoc aa | 674.6 g | + |
| 4 | DIPCDI | 276 mL | 120' |
| Control by Chloranyl if − continue if + follow step 1 | | | |
| 5 | DMF | 3 | 1' |
| 6 | Pip/DMF 20% | 1 | 1' |

-continued

| Step | Reagent | Repetitions | Time |
|---|---|---|---|
| 7 | Pip/DMF 20% | 1 | 5' |
| 8 | DMF | 4 | 1' |

Programme for incorporation of Fmoc-Leu (3)
f = 0.85    200 g resin    Excess 3 eq.    MW 353.4

| 1 | HOBt 0.25 M | 3 | 1' |
|---|---|---|---|
| 2 | Fmoc aa | 184 g | + |
| 3 | HOBt | 78 g | + |
| 4 | DIPCDI | 89.1 mL | 120' |

Control by ninhydrine if + more time if + follow step 4

| 5 | DMF | 3 | 1' |
| 6 | Pip/DMF 20% | 1 | 1' |
| 7 | Pip/DMF 20% | 1 | 5' |
| 8 | DMF | 4 | 1' |

Programme for incorporation of Fmoc-D-Ser(Tbu) (4)
f = 0.85    200 g resin    Excess 2 eq.    MW 383.4

| 1 | HOBt 0.25 M | 3 | 1' |
|---|---|---|---|
| 2 | Fmoc aa | 124.5 g | + |
| 3 | HOBt | 48.6 g | + |
| 4 | DIPCDI | 55.3 mL | 120' |

Control by ninhydrine if + more time if + follow step 4

| 5 | DMF | 3 | 1' |
| 6 | Pip/DMF 20% | 1 | 1' |
| 7 | Pip/DMF 20% | 1 | 5' |
| 8 | DMF | 4 | 1' |

Programme for incorporation of Fmoc-D-Tyr(2ClTrt) (5)
f = 0.85    200 g resin    Excess 2 eq.    MW 680

| 1 | HOBt 0.25 M | 3 | 1' |
|---|---|---|---|
| 2 | Fmoc aa | 220 g | + |
| 3 | HOBt | 48.6 g | + |
| 4 | DIPCDI | 55.3 mL | 120' |

Control by ninhydrine if + more time if + follow step 4

| 5 | DMF | 3 | 1' |
| 6 | Pip/DMF 20% | 1 | 1' |
| 7 | Pip/DMF 20 % | 1 | 5' |
| 8 | DMF | 4 | 1' |

Programme for incorporation of Fmoc-Ser(Trt) (6)
f = 0.85    200 g resin    Excess 2 eq.    MW 569

| 1 | HOBt 0.25 M | 3 | 1' |
|---|---|---|---|
| 2 | Fmoc aa | 185.3 g | + |
| 3 | HOBt | 48.6 g | + |
| 4 | DIPCDI | 55.3 mL | 120' |

Control by ninhydrine if + more time if + follow step 4

| 5 | DMF | 3 | 1' |
| 6 | Pip/DMF 20% | 1 | 1' |
| 7 | Pip/DMF 20% | 1 | 5' |
| 8 | DMF | 4 | 1' |

Programme for incorporation of Fmoc-Trp (7)
f = 0.85    200 g resin    Excess 2 eq.    MW 426.5

| 1 | HOBt 0.25 M | 3 | 1' |
|---|---|---|---|
| 2 | Fmoc aa | 138.6 g | + |
| 3 | HOBt | 48.6 g | + |
| 4 | DIPCDI | 55.3 mL | 120' |

Control by ninhydrine if + more time if + follow step 4

| 5 | DMF | 3 | 1' |
| 6 | Pip/DMF 20% | 1 | 1' |
| 7 | Pip/DMF 20% | 1 | 5' |
| 8 | DMF | 4 | 1' |

Programme for incorporation of Fmoc His(Mmt) (8)
f = 0.85    200 g resin    Excess 2 eq.    MW 650

| 1 | HOBt 0.25 M | 3 | 1' |
|---|---|---|---|
| 2 | Fmoc aa | 210.6 g | + |
| 3 | HOBt | 48.6 g | + |
| 4 | DIPCDI | 55.3 mL | 120' |

Control by ninhydrine if + more time if + follow step 4

| 5 | DMF | 3 | 1' |
| 6 | Pip/DMF 20% | 1 | 1' |
| 7 | Pip/DMF 20% | 1 | 5' |
| 8 | DMF | 4 | 1' |

Programme for incorporation of Pyr (9)
f = 0.85    200 g resin    Excess 2 eq.    MW 129.1

-continued

| Step | Reagent | Repetitions | Time |
|---|---|---|---|
| 1 | HOBt 0.25 M | 3 | 1' |
| 2 | Aa | 41.9 g | + |
| 3 | HOBT | 48.6 g | |
|   | DIPCDI | 55.3 mL | 45' |

Control by ninhydrine if + more time if + follow step 4

| 4 | DMF | 4 | 1' |
| 5 | MeOH | 3 | 1' |
| 6 | Ether | 4 | 1' |
| 7 | Dry in the lyophiliser | | |

Once the resin has been dried it is weighed, giving 539.5 of final peptidyl-resin which implies a quantitative synthetic yield, taking into account the initial functionalisation of the Fmoc-Pro-peptidyl resin, of 0.85 meq/g.

EXAMPLE 6

Release of the Peptide from the Resin. Production of Pyr-His-Trp-Ser(Trt)-Tyr(2ClTrt)-D-Ser(tBu)-Leu-Arg-Pro-COOH.

38.7 g of completely dry peptidyl-resin (funct. 0.337 meq/g) obtained in example 5 are treated with 560 mL of AcOH/TFE/DCM (1:2:7) for 1 hour and 30 minutes at room temperature. Then the mixture is washed twice with 75 mL of AcOH/TFE/DCM (1:2:7) and twice with diethyl ether, filtered and the dissolvent evaporated off. The solid is dried under vacuum to proceed with the synthesis following the step described in example 7.

EXAMPLE 7

De-Protection of the Side Chains. Production of Pyr-His-Trp-Ser-Try-D-Ser(tBu)-Leu-Arg-Pro-COOH.

The solid from example 6 is treated with 451 mL of TFA-DCM (2:98 v/v) for 1 hour 30 minutes. It is then precipitated over diethyl ether. It is filtered and washed six times with diethyl ether. In this way 15.9 g of gosereline or busereline unprotected precursor are obtained with the exception of the side chain of the D-Ser which is alkylated as an ether of tert-butyl.

EXAMPLE 8

Production of the Ethylamine/HOBt Salt 11.58 g (77.2 mmol) of HOBt are weighed out in a 2-L flask. 1 L of water is added and the flask submerged in an ultrasound bath until dispersion is complete. 6.18 mL (103.1 mmol) of ethylamine are added, maintaining the ultrasonification. The dispersion is seen to dissolve completely. The transparent solution is allowed to stand for 5 minutes at room temperature. It is then frozen in a bath of dry ice and acetone. It is lyophilised. Once well lyophilised the product is withdrawn from the flask and collected in a beaker. The solid is left to dry under vacuum in the presence of KOH for at least 24 hours, to give 15.1 g of the salt of ethylamine/HOBt.

EXAMPLE 9

Conversion to Ethylamide. Production of Pyr-His-Trp-Ser-Tyr-D-Ser(tBu)-Leu-Arg-Pro-CO—NH—CH2—CH3

10.45 g of precursor (8.61 mmol) are dissolved in 360 mL of DMF. 5.2 g (3 eq) of the well dried ethylamide salt with HOBt is added and homogenised in an ultrasound bath. 3.6 mL of DIPCDI (3 eq) are added with magnetic stirring and the reaction maintained at 50° C. for 6 hours. It is evaporated to dryness until an oil is obtained. To this 30 mL of $CH_3CN$ are added and the mixture homogenised in the ultrasound bath and 100 mL of water are added to the ultrasound bath. A white coloured suspension is obtained which is frozen and lyophilised. The solid obtained with quantifiable yield is purified using preparative HPLC on a reverse-phase $C_8$ column, with isocratic elution with $CH_3CN/H_2O$ at 0.1% TFA, obtaining an overall yield for the synthesis and purification of 44%.

EXAMPLE 10

Conversion to Azaglycinamide. Production of Pyr-His-Trp-Ser-Tyr-D-Ser(tBu)-Leu-Arg-Pro-CO—NH—NH—CO—NH2

Pyr-His-Trp-Ser-Tyr-D-Ser(tBu)-Leu-Arg-Pro-CO—NH—CH2—CH3 (13 g, 10.72 mmol) are dissolved in 80 mL of DMF. 8 g of PyBOP (3 eq) are weighed out and dissolved in 20 mL of DMF.

1.79 g of semicarbacide chlorohydrate $H_2NCONHNH_2 \cdot HCl$ (1.5 eq) and 25 mL of DMF and 2.82 mL (1.6 eq) of DIEA are added. The initial suspension is sonicated until completely dissolved.

To the peptide solution and under stirring the solution with PyBOP is added. Later, DIEA (5.26 mL; 3 eq) are added. Next, the dissolved semicarbacide is added and the reaction allowed to proceed for 5 hours. After this time the reaction is precipitated over 1 L of cooled diethyl ether. After 10 minutes the suspension is filtered under vacuum, washed repeatedly with diethyl ether and ground to give a quantitative yield of white solid which is subsequently purified using preparative HPLC on an reverse-phase $C_8$ column, with isocratic elution with $CH_3CN/H_2O$ at 0.1% TFA, to obtain an overall synthesis and purification yield of 38.3%.

What is claimed is:

1. A procedure for solid phase peptide synthesis (SPPS), following a linear or covergent strategy, wherein the peptides contain the sequence of general formula (I):

where 30>n>1
wherein
30>n>1;
Y=H—, $(C_1-C_{20})$ alkyl or $(C_1-C_{20})$ acyl;
X=—OH, —$NHCH_3$, —$NHCH_2CH_3$, —NH—$C_aH_b$ (10>a>2 and 18>b>5), —$NHCF_3$, —$NHCH_2CF_3$, —NH—$C_aH_bF_f$ (10>a>2, 18>b>5, 9>f>0), —NH—$C_cH_dO_e$ (c, d and e>1) or —NH—NR—CO—$NH_2$ (where R represents the side chains of any amino acid);
$A_n$ (30>n>1) can be any natural of synthetic amino acid, including pyroglutamic acid, provided the sequence contains a minimum of one amino acid with the side chain acylated or alkylated, with a tert-butyl or tert-butoxycarbonyl group;
as well as all pharmaceutically acceptable salts, for the peptide, formed by addition of acids or complexes thereto, which procedure comprises:
   a) the use of amino acids with the Nα group protected, through the use of temporary protector groups labile to treatment with basic solutions;
   b) protecting the side chains of those amino acids which have the chain alkylated or acylated in the final product, with labile protectors stable to acid solutions of type 1 and 2, wherein type 1 solutions are selected from solutions of acetic acid in proportions ranging from 1 to 30% in a solvent, solutions of hexafluoroisopropanol in a solvent different from that used in forming the acetic acid solutions, and equivalent acid solutions, and type 2 solutions are selected from solutions of acetic acid in proportions greater than 30% in a solvent different than that used in the type 1 solutions, solutions of trifluoroacetic acid in proportions lower than 5% in solvents different than those used to form the type 2 acetic acid solutions, and equivalent acid solutions;
   c) protecting the side chains of at least one of the amino acids that has the chain in free form in the final product, with hyperlabile protectors which are stable to treatment with acid solutions of type 1 and labile to treatment with acid solutions of type 2 indicated above; and
   d) using a polymeric support that provides peptide-resin bonds which are labile to treatment with acid solutions of type 1 or type 2 indicated above.

2. A procedure according to claim 1 characterized because the hyperlabile protectors used for the side chains of some amino acids are preferably methyltrityl or methoxytrityl for histidine, trityl or chlorotrityl for tyrosine, methyltrityl or trityl for lysine and trityl for aspartic acid, glutamic acid, threonine, and serine.

3. A procedure according to claim 1 characterized because the labile protectors used for those amino acids whose lateral chain is protected in the final product are preferably tert-butyl or tert-butoxycarbonyl.

4. A procedure according to claim 1, characterized because polymeric supports are used which provide peptide-resin bonds labile to treatment with said type-1 acid solutions such as resins of the chlorotrityl, trityl, methyltrityl or methoxytrityl type.

5. A procedure according to claim 1, characterized because when X=OH is comprises the following steps:
   i) Incorporation of the first amino acid protected onto the polymeric support through the use of conventional coupling methods commonly used in the art;
   ii) Linear growth of the peptide chain using hyperlabile protectors for the side chains of at least one of those amino acids that has its chain free in the final product and labile protector(s) for the amino acid(s) that is/are alkylated or acylated in the final product; and
   iii) Cleavage of the peptide-resin bond through treatment with type-1 acid solutions to obtain the protected precursor.

6. A procedure according to claim 1, characterized because when X≠OH it comprises the following steps:
   i) Conversion of the precursor obtained in step iii of claim 5, which contains labile and hyperlabile protecting groups on the lateral chains of some amino acids, to give rise to the final protected product; and
   ii) Elimination of the hyperlabile protecting groups present in the peptide by means of treatment with type-2 acid solutions to obtain the final product.

7. A procedure according to claim 6, characterized because when X≠OH it comprises the same steps as when X=OH and, additionally, the following steps:
   i) Elimination of the hyperlabile protecting groups present in the peptide by means of treatment with type-2 acid solutions to obtain the final product; and
   ii) Conversion of the precursor obtained in the previous step, which only contains labile protecting groups on the lateral chains of some amino acids, to give rise to the final protected product.

8. A procedure for the synthesis of gosereline according to claim 1, characterized because it consists of the following steps:
   i) Coupling of Fmoc-Pro-OH onto the resin 2-chlorotrityl and subsequent linear growth of the peptide chain through coupling of Fmoc-Arg(HCl), Fmoc-Leu, Fmoc-D-Ser(tBu), Fmoc-Tyr(ClTrt), Fmoc-Ser(Trt), Fmoc-Trp, Fmoc-His(Mmt) and pyroglutamic acid;
   ii) Breakage of the peptide-resin bond through treatment with type-1 acid solutions to obtain the protected precursor;
   iii) Elimination of the hyperlabile protecting groups present in the protected precursor through treatment with type-2 acid solutions; and iv) Conversion of the precursor through formation of an active ester thereof and subsequent coupling of semicarbacide chlorohydrate with in situ neutralization to give rise to gosereline.

9. A procedure for the synthesis of gosereline according to claim 8, characterized because the procedure is interrupted at step ii) and the following steps subsequently carried out:
   i) Conversion of the precursor, with all or some of the tri-functional amino acids which will have the free side chain in the final product protected, through formation of an active ester thereof and subsequent coupling of semicarbacide chlorohydrate with in situ neutralization to give rise to protected gosereine; and
   ii) elimination of the hyperlabile protecting groups present in the protected gosereline through treatment with type-2 acid solutions.

10. A procedure for the synthesis of busereline according to claim 1, characterized because it consists of the following steps:
   i) Coupling of Fmoc-Pro-OH onto the 2-chlorotrityl resin and subsequent linear growth of the peptide chain through coupling of Fmoc-Arg(HCl), Fmoc-Leu, Fmoc-D-Ser(tBu), Fmoc-Tyr(ClTrt), Fmoc-Ser(Trt), Fmoc-Trp, Fmoc-His(Mmt) and pyroglutamic acid;
   ii) Breakage of the peptide-resin bond through treatment with type-1 acid solutions to obtain the protected precursor;
   iii) Elimination of hyperlabile protecting groups present in the protected precursor through treatment with type-2 acid solutions; and
   iv) Conversion of the precursor through formation of an active ester thereof and subsequent coupling of the salt of HOBt of ethylamine to give rise to busereline.

11. A procedure for the synthesis of busereline according to claim 10, characterized because the procedure is interrupted at step ii) and the following steps subsequently carried out:
   i) Conversion of the precursor, with all or part of the tri-functional amino acids which the side chain will have free in the final product, through the formation of an active ester thereof and subsequent coupling of the salt of $HOB_t$ of the ethylamine to give rise to the protected busereline; and
   ii) Elimination of the hyperlabile protecting groups present in the protected gosereline through treatment with type-2 acid solutions.

* * * * *